US006894023B1

(12) United States Patent
Junker et al.

(10) Patent No.: US 6,894,023 B1
(45) Date of Patent: May 17, 2005

(54) GROWTH HORMONE CRYSTALS AND A PROCESS FOR PRODUCTION OF THESE GH-CRYSTALS

(75) Inventors: Flemming Junker, Humlebæk (DK); Claus Friis Theisen, København (DK)

(73) Assignee: Novo Nordisk A/S, Bagsvaerd (DK)

( * ) Notice: Subject to any disclaimer, the term of this patent is extended or adjusted under 35 U.S.C. 154(b) by 346 days.

(21) Appl. No.: 09/592,032

(22) Filed: Jun. 12, 2000

Related U.S. Application Data

(63) Continuation of application No. 09/063,749, filed on Apr. 21, 1998, now Pat. No. 6,117,984, which is a continuation of application No. 08/350,758, filed on Dec. 7, 1994, now Pat. No. 5,780,599, which is a continuation of application No. 08/222,515, filed on Apr. 1, 1994, now abandoned, which is a continuation of application No. 07/961,932, filed as application No. PCT/DK91/00203 on Jul. 12, 1991, now abandoned.

(30) Foreign Application Priority Data

Jul. 13, 1990 (DK) .............................. 1687/90

(51) Int. Cl.⁷ .............................. A61K 38/18
(52) U.S. Cl. .................. 514/2; 530/399; 530/420; 530/422; 530/305
(58) Field of Search .................. 514/12; 530/399, 530/420, 422, 305

(56) References Cited

U.S. PATENT DOCUMENTS 2,174,862 A    10/1939   Sahyun ........................ 167/75
5,780,599 A *  7/1998   Junker et al. ................ 530/399

FOREIGN PATENT DOCUMENTS

| EP | 0 177 478 | 4/1986 |
| EP | 0 216 485 | 4/1987 |
| EP | 0 277 03  | 8/1988 |
| EP | 0 343 696 | 11/1989 |
| EP | 0 355 460 | 2/1990 |

OTHER PUBLICATIONS

Bell et al., J. Biol. Chem., vol. 260, No. 14, pp. 8520–8525 (1985).
J. Clarkson et al., J. Mol. Biol. vol. 208, pp. 719–721 (1989).
Bell et al., J. Biol. Chem., vol. 260, No. 14, pp. 8520–8525 (1985).
J. Clarkson et al., J. Mol., Biol., vol. 208, pp. 719–721 (1989).

\* cited by examiner

*Primary Examiner*—Karen Cochrane Carlson
*Assistant Examiner*—Samuel Wei Liu
(74) *Attorney, Agent, or Firm*—Richard W. Bork, Esq.; Marc A. Began, Esq.; Reza Green, Esq.

(57) ABSTRACT

A process for producing cation crystals of growth hormone or growth hormone derivatives, as well as growth hormone and growth hormone derivatives. The process of producing the growth hormone crystals includes the steps of (a) adding cations of inorganic or organic nature and an organic solvent or a mixture of inorganic solvents at a pH between 5.0 and 6.8 to a solution of growth hormone or derivatives. (b) growing growth hormone crystals at a temperature from about 0 to 30° C. and (c) isolating the cation crystals.

21 Claims, 1 Drawing Sheet

1

GROWTH HORMONE CRYSTALS AND A PROCESS FOR PRODUCTION OF THESE GH-CRYSTALS

CROSS-REFERENCE TO RELATED APPLICATIONS

Figure 1:
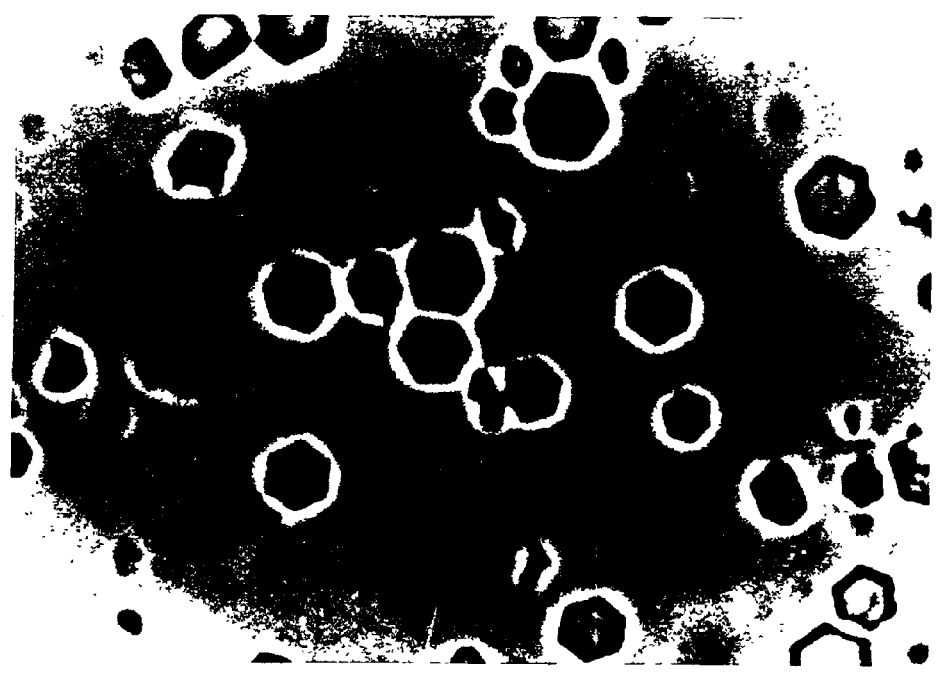

The present application is a continuation of application Ser. No. 09/063,749, filed on Apr. 21, 1998, which is now U.S. Pat. No. 6,117,984, which is a continuation of application Ser. No. 08/350,758, filed on Dec. 7, 1994, which is now U.S. Pat. No. 5,780,599, which is a continuation of application Ser. No. 08/222,515, filed on Apr. 1, 1994, now abandoned, which is a continuation of application Ser. No. 07/961,932, filed on Jan. 13, 1993, now abandoned, which is a filing under 35 U.S.C. 371 of PCT/DK91/00203, filed on Jul. 12, 1991, and which claims priority under 35 U.S.C. 119 of Danish application serial no. 1687/90, filed on Jul. 13, 1990, the contents of each of which are fully incorporated herein by reference.

FIELD OF INVENTION

The present invention concerns a method of producing growth hormone crystals in the presence of cations, novel growth hormone (GH) crystals and pharmaceutical preparations containing such novel crystals.

BACKGROUND OF THE INVENTION

The growth hormones (GH) from man and from the common domestic animals are proteins of approximately 191 amino acids, synthesized and secreted from the anterior lope of the pituitary. The growth hormone is a key hormone involved in the regulation of not only somatic growth, but also in the regulation of metabolism of proteins, carbohydrates and lipids.

During the past 40 years or more much attention has been devoted to the unravelling of the biochemical function of the growth hormones from various species. The reason for this interest in the molecular function of this protein rests upon the commercial interests from both veterinarian and medical circles. The GH gene has now been cloned and human growth hormone (hGH) and Met-hGH are currently beeing produced biosynthetically by the use of both bacteria and mammalian cell cultures.

Pharmaceutical preparations of GH tend to be unstable. Degradation products such as deamidated or sulfoxydated products and dimer or polymer forms are generated—especially in solutions of GH. Therefore, today GH is lyophilized and stored in the lyophilized form at 4° C. until it is reconstituted by the patient, before start of use.

The reconstituted preparations are preferably stored at 4° C. to minimize degradation in solution. However some degradation will take place during such storage which can be for a period of up to about 14 days. There is thus a need in the art for more stable preparations of GH.

It would also be an advantage to avoid the lyophilization step in the production of GH preparations. Lyophilization is a time consuming and costly process and also often a limiting procedure due to the capacity of the freeze drier.

The present invention is based on the surprising recognition that the above needs are fulfilled by means of a crystallization step in the production of GH.

Although readily available in quantities sufficient for crystallization, GH has so far eluded succesfull crystallization. Micro crystals, or amorphous material have been reported from a variety of sources: (Jones et al., Bio-Technology (1987) 5, 499–500; Wilhelmi et al., J.Biol.Chem. (1984) 176, 735–745; Clarkson et al., J.Mol.Biol. (1989) 208, 719–721; Bell et al., J.Biol.Chem. (1985) 260, 8520–8525 and V. L. Spitsberg, Analytical Biochemistry, 1987, 160, 489–435)

The hanging drop method is the most common method in use for this purpose. Apparently due to heterogenicity among growth hormone preparations the size and the shape of the crystals have been reported to vary significantly. The largest crystals have been reported by Jones et al. (1987). For their successfull experiments they used a mixture of polyethylene glycol 3500 and beta octyl glucoside at neutral pH. Clarkson et al. (1989) reported that the use of lower alcohols and acetone permitted the generation of crystals of 0.001 to 0.005 cubic mm with varying shapes. None of the known methods are however suitable for commercial production of GH crystals a.o. due to the fact that growth times of from several weeks up to one year are needed.

Bovine growth hormone has been formulated for veterinarian use in a mixture of divalent ions and an oil (EP 343 696). By addition of $ZnCl_2$ to either bovine or ovine growth hormone in the presence of lipids undefined particles were produced to form a prolonged release formulation. The growth hormone was dispersed in the carrier in such a way as to trap 1 to 4 Zinc molecules per growth hormone molecule. The solutions were prepared in the presence of varying concentrations of denaturing solutes (1 to 4 M of urea) at high pH (9.5). A reproduction of this process with hGH has shown that it is not possible to produce crystals in this way.

From the literature it is well known that the presence of divalent cations during the process of crystallization permits not only excellent orientation during analysis, but also improved physical conditions for the crystallization of insulin (e.g. U.S. Pat. No. 2,174,862). Growth hormone is, however, more than three times larger than insulin and has a totally different conformation. Surprisingly the addition of cations to solutions containing hGH have now permitted the generation of stable, uniform crystals of the growth hormone in high yields. Furthermore, the time used for the formation of high quality hGH crystals is relatively short.

SUMMARY OF THE INVENTION

In its broadest aspect the present invention is related to a process for production of cation crystals of GH or GH derivatives, comprising the following steps:

a) to a solution of GH or derivatives thereof is added cations of inorganic or organic nature and an organic solvent or a mixture of organic solvents at a pH between 5.0 and 6.8, b) growing of crystals at a temperature from about 0 to about 30° C., and c) isolation of the cation crystals by known means.

In the present context GH is intended to cover all species of GH including human, bovine, porcine, ovine, salmon, trout or tuna. GH derivatives are intended to cover GH of human or animal species with minor variation in the protein sequence. Thus a few amino acid residues may have been deleted or replaced by other amino acid residues. Also covered is truncated forms of growth hormone and derivatives thereof as well as growth hormones with amino acid residues added to the N- and/or C-terminal end of the protein, such as Met-hGH.

The process according to the present invention has for the first time made it possible to produce chemically stable and uniform cation-GH crystals. Also, the present process enables production of both larger and smaller crystals of growth hormone, as the need may be.

The pH in step a) is preferably 5.8 to 6.5, and most preferably from 6.0 to 6.5.

According to a preferred embodiment of the present invention the growth hormone is of human nature.

The cations may be of inorganic or organic nature. Divalent cations are preferred and of these an inorganic cation such as $Zn^{++}$ has turned out to be well suited for the fast formation of stable GH crystals. Also mixtures of these cations can be used. The cation should be added in an amount providing fast and efficient formation of well defined crystals. The upper limit for the amount of added cation is the amount which would cause unspecific precipitation of substantial amounts of amorpheous material.

If $Zn^{++}$ is used, suitable concentrations will typically be from about 0.2 to 10 mol $Zn^{++}$/mol GH. However, if the crystallization reaction mixture contains a buffer or other compound which is capable of binding some of the. cation, e.g. in a complexed form, greater concentration of the cation will be needed because some of the cation will not be available for the crystallization process.

$Zn^{++}$ will preferably be used in an amount which will cause formation of GH crystals with a molar ratio between $Zn^{++}$ and GH from about 0.2 to about 10, preferably from about 0.5 to about 5 and more preferably from about 0.5 to about 2.

In a preferred embodiment of the invention the organic solvent added in step a) may be chosen from the group consisting of short chained aliphatic, cyclic or aromatic alcohols and ketones. Suitable organic solvents are acetone, methanol, ethanol and 2-propanol. A preferred organic solvent is ethanol or acetone. The concentration of the organic solvent may be from 0.1 to 50% v/v, preferably from 0.1 to 30%, more preferably from 0.1 to 20%, even more preferably from 5 to 15% and most preferred from 6 to 12% v/v.

The present process may be used as a fast and efficient down stream processing of the growth hormone in question, due to the formation of crystals in large volumes of solutions.

The present invention is also related to novel cationic crystals of GH or GH derivatives.

The crystals are preferably hGH crystals or crystals of derivatives of hGH. The cation is preferably $Zn^{++}$ and the molar ration between $Zn^{++}$ and GH will typically be from about 0.2 to 10, preferably from 0.5 to 5 and more preferably from 0.5 to 2.0. The size of the crystals will be dependent on the $Zn^{++}$ to GH ratio and the choice and content of solvent used in the process. hGN crystals according to the present invention have been shown to have a biological potency similar to that of a solubilized hGH standard in in vitro and in vivo tests. The novel GH crystals can thus be used for the same indications as the commercially available hGH preparation.

Pharmaceutical preparations containing the novel GH crystals will typically be solutions or suspensions and may contain the usual adjuvants and additives used for pharmaceutical hGH preparations, such as buffers, glycerol and preservatives. The preparations may be administered in the same way as the commercial hGH preparations. The crystals may also be formulated as dried crystals which will then have to be reconstituted before start of use.

The pharmaceutical preparations containing the novel GH crystals have surprisingly a very high chemical stability compared with preparations made from commercially available GH.

The present invention therefore provides for a possibility of production of pharmaceutical preparations that are more convenient, especially for the patients. Due to the high stability of the crystals in suspension, the present invention will as an example make it possible to produce ready to use pharmaceutical preparations in the form of suspensions which will not need to be reconstituted by the patients before use.

In a further aspect the invention provides a valuable tool for production and purification purposes of GH.

FIG. 1 is a photomicrograph of human growth hormone crystals formed by the method of the invention.

DETAILED DESCRIPTION OF THE INVENTION

The starting material, the growth hormone that may be of any origin and if desired derivatized in solution, is adjusted to a concentration preferably greater than about 0.1 mg/ml, more preferably from about 4 to about 7 mg/ml and most preferred about 6 mg/ml. The pH will preferably be from 6.0 to 6.3.

To the above mentioned solution may be added an organic solvent. A preferred organic solvent is ethanol in a concentration which may vary between 0,1 and 20%, preferably 5 and 15%, and most preferred 6 and 12%.

Other solvents such as acetone, methanol or propanol may be used alone or as a mixture instead of or together with ethanol in a concentration within the range of from 1 to 50%.

Cations of inorganic or organic nature, or mixtures thereof are then added to the resulting solution.

A preferred cation is $Zn^{++}$ which will normally be used in a concentration from 0.5 to 10 mol/mol GH, preferably from 1.0 to 3.0 mol/mol GH, more preferred from 1.1 to 2.2 mol/mol GH and most preferred from 1.2 to 2.0 mol/mol GH.

If cations of inorganic nature other than $Zn^{++}$ are used, the concentration may be varied between 0.5 and 10 mol/mol GH.

The crystals are then grown for a period of from 1 to 120 hrs. preferably 5–72 hrs., most preferred 20–48 hrs., and at a temperature of between 0 and 30° C., preferably from 4 to 25° C.

The crystals may be recovered by centrifugation or filtration, followed by washing and/or freeze drying to remove remaining organic solvents.

Pharmaceutical preparations of dried crystals or crystals in suspension can now be formulated by using various selected buffers and other pharmaceutically acceptable additives.

The invention is further illustrated but not limited by the following examples:

EXAMPLE 1

Crystallization of hGH in the Presence of $Zn^{++}$ 500 ml of hGH solution produced according to H. Dalbøge et al., Bio-Technology (1987), 5, 161–164, in a concentration of 6 mg/ml was incubated in 10 mM phosphat buffer ($NaH_2PO_4$) and adjusted to pH 6.1 with $H_3PO_4$. Acetone was added to a final concentration of 10% (v/v) and thereafter zinc acetate solution was added to a final concentration of 0.08 mg $ZnAc_2$, $2H_2O$/ml~1.34 mol $Zn^{++}$/mol hGH.

The resulting solution was left at 15° C. for 20 hours, whereby crystals were allowed to form.

After this the crystals were recovered and washed 3 times with crystallization buffer without acetone. The crystallization was checked by microscopy and the size of the crystals were measured to 8–12 μm. A photomicrograph is shown in FIG. 1.

The crystal yield of hGH was determined by solubilization of the washed crystals in 7M urea followed by ion exchange HPLC analysis.

The yield was found to be more than 50%.

EXAMPLE 2

Example 1 was repeated with the exception that Met-hGH was used instead of hGH. The crystals recovered by this process were identical in shape and size to those obtained with hGH. The yield was more than 50%.

EXAMPLE 3

Example 1 was repeated with the exception that the addition of acetone was omitted.

The crystals of hGH resulting from this procedure were much smaller than the crystals resulting from Example 1, less than 2 μm.

EXAMPLE 4

Example 1 was repeated under conditions where acetone was exchanged with ethanol and temperature during growing period was. 20° C. instead of 15° C. All other experimental conditions were identical to those described in example 1. By varying the ethanol concentration the optimal concentration was found to be 7.5% (v/v). The yield was increased to >80% if the motherfluid following initial crystallization for 16 hrs was supplemented with further 4% (v/v) ethanol and the crystallization temperature was lowered from 20° to 10° C. over a period of 16 hrs. The size of the crystals were between 3 to 6 μm with a shape similar to that described in example 1.

EXAMPLE 5
Determination of the Amount of Zn Bound in hGH Crystals

Example 1 was repeated with the exception that ethanol in a concentration of 7.5% (v/v) was added instead of acetone and that crystals were allowed to form for 16 hrs at 20° C., then the crystals were separated from the motherfluid by centrifugation and washed once with 10 mM phosphate buffer. The crystals were solubilized by raising the pH to 8.0 with NaOH. The hGH was measured by ion exchange HPLC or by UV determination. The Zn concentration was measured by atomic absorption and the results were compared with those values obtained for the total crystal suspension. The ratio of bound Zn to hGH was found to be 1.9 mole of Zn per mole of hGH.

EXAMPLE 6
Formulation of a Pharmaceutical Preparation Containing hGH

Crystals were grown as described in example 5 and stored at 4° C. The crystals were then isolated by centrifugation and subsequent removal of the motherfluid. Then the crystals were freeze dried over night to achieve dry crystals with no remaining organic solvent. A pharmaceutical suspension of the dried crystals was prepared according to the following formulation:

| | |
|---|---|
| hGH crystals | 1.3 mg/ml |
| $NaH_2PO_4,2H_2O$ | 3.0 mg/ml |
| $Zn(Ac)_2,H_2O$ | 0.1 mg/ml |
| Glycerol | 15.0 mg/ml |
| Benzyl alcohol | 15.0 mg/ml | pH was adjusted to 6.2

EXAMPLE 7

Example 6 was repeated with the exception that $Zn(Ac)_2$ $H_2O$ was omitted, giving a suspension of the following formulation:

| | |
|---|---|
| hGH crystals | 1.3 mg/ml |
| $NaH_2PO_4,2H_2O$ | 3.0 mg/ml |
| Glycerol | 15.0 mg/ml |
| Benzyl alcohol | 15.0 mg/ml | pH was adjusted to 6.2

EXAMPLE 8

The crystals were treated in the same way as in example 6 and the following suspension was formulated:

| | |
|---|---|
| hGH crystals | 1.3 mg/ml |
| $NaH_2PO_4,2H_2O$ | 2.5 mg/ml |
| NaCl | 5.7 mg/ml |
| Benzyl alcohol | 15.0 mg/ml | pH was adjusted to 6.2

EXAMPLE 9

The crystals were treated in the same way as in example 6 and the following solution was prepared:

| | |
|---|---|
| hGH crystals | 1.3 mg/ml |
| $NaH_2PO_4,2H_2O$ | 2.14 mg/ml |
| NaCl | 9.0 mg/ml | pH was adjusted to 6.1

EXAMPLE 10
Tibia Test

To estimate the in vivo biological potency of the hGH crystals prepared according to the invention a tibia test was performed using hypophysectomized rats. The test was performed in accordance with the method described in the European Pharmacopoeia.

Two preparations of hGH crystals produced according to example 1 and formulated as preparations according to exampel 9 (F-7 and F-8) each containing an estimated amount equivalent to 4 IU were tested against a dissolved standard hGH preparation.

The following results were obtained:

TABLE 1

The potency of the preparations F-7 and F-8

| Test preparat. | Potency % of std. | IU/vial | 95% confid. limits, % of std. |
|---|---|---|---|
| F-7 | 90.1 | 3.9 | 87.6–114.1 |
| F-8 | 103.8 | 4.5 | 90.6–110.4 |
| Std. hGH 1986 | ≡100.0 | ≡4.4 | — |

From the performed test it can be concluded that the hGH crystals according to the invention are equally biological potent as the solubilized hGH standard and therefore will have a bioavailability equal to that of usual solubilized hGH.

EXAMPLE 11 hGH crystals were grown as described in example 5. Immediately before use a suspension was prepared by centrifugation of the crystals, subsequent removal of the motherfluid, and resuspension of the crystals in sterile 10 mM $NaH_2PO_4$, pH 6.2 giving a final concentration of 0.16 mg hGH/ml suspension.

The suspension was used to estimate the potency of the hGH crystal preparation in a weight gain assay. The test was performed in accordance with the method described in the European Pharmacopoeia, with the exception that the time of dosing was prolonged to 10 days in order to optimize the biological response.

Two preparations of hGH crystals were used, each containing the same amount of hGH protein as the preparations of a growth hormone standard, which they were tested against. The standard was a reconstituted freeze-dried hGH preparation. All the animals received the same amount of hGH.

The potency of the hGH crystal preparations were found to be 92.6% of the standard. The 95% confidence limits were 79.1–126.4% of the standard.

The hGH crystal preparation was thus shown to have a biological potency equal to that of the solubilized hGH standard.

EXAMPLE 12

Stability of hGH crystals stored in suspension for 6 months at 22–24 °C.

The crystals were formed as described in Example 1 with the exception that 7.5% (v/v) acetone was added instead of 10% (v/v).

The crystals were allowed to remain in suspension in the mother fluid for 6 months at 22–24° C. A sample of hGF crystals were removed by centrifugation, washed once with crystallization buffer without acetone and solubilized by raising the pH to 8.0.

The solublized hGH crystals were subjected to analysis on ion exchange HPLC and GPC for detection of desamido and split forms or dimers and polymers, respectively.

When the data were compared with those of a reconstituted lyophilized hGH preparation stored at 25° C. for 32 days the content of the main peak of hGH in reconstituted hGH crystals was superior to reconstituted lyophilized hGH, stored under comparable conditions (see table 2).

TABLE 2

| Storage | Reconstituted hGH 25° C. 32 days | Crystals 22–24° C. 6 months |
|---|---|---|
| Main peak on IE-HPLC (%) | 71.2 | 92.3 |
| Dimer (%) | 0.7 | 1.2 |
| Polymer (%) | 0.3 | 0.3 |
| Desamido (%) | 25.9 | 5.0 |
| Didesamido (%) | 2.9 | 1.8 |
| Split form (%) | — | — |

What is claimed is:

1. Isolated cation crystals of human growth hormone (hGH) or a hGH derivative.

2. A pharmaceutical preparation comprising crystals according to claim 1.

3. A process for production of cation crystals of growth hormone (GH) or of a GH derivative, said process comprising the following steps:
   a) adding to a solution of said GH or said GH derivative inorganic or organic cations and an organic solvent or a mixture of organic solvents at a pH between 5.0 and 6.8,
   b) growing of crystals at a temperature from about 0 to about 30° C., and
   c) isolating the cation crystals grown in step b).

4. A process according to claim 3, wherein the pH in step a) is from 5.8 to 6.5.

5. A process according to claim 3, wherein the organic solvent is selected from the group consisting of short chain aliphatic alcohols, cyclic alcohols, aromatic alcohols and ketones.

6. A process according to claim 5, wherein the organic solvent is selected from the group consisting of acetone, methanol, ethanol and 2-propanol.

7. A process according to claim 6, wherein the organic solvent is ethanol or acetone.

8. A process according to claim 3 wherein the organic solvent is added in a concentration of about 0.1 to about 50% v/v.

9. A process according to claim 8, wherein the organic solvent is added in a concentration of from 0.1 to 30% v/v.

10. A process according to claim 8, wherein the organic solvent is added in a concentration of from 0.1 to 20% (v/v).

11. A process according to claim 8, wherein the organic solvent is added in a concentration of from 5 to 15% (v/v).

12. A process according to claim 8, wherein the organic solvent is added on a concentration of from 6 to 12% (v/v).

13. A process according to claim 3, wherein the cation is a divalent cation.

14. A process according to claim 13, wherein the divalent cation is $Zn^{++}$.

15. A process according to claim 14, wherein $Zn^{++}$ is added in a concentration from 0.5 to 10 mol $Zn^{++}$/mol GH.

16. A process according to claim 15 wherein the concentration of $Zn^{++}$ is from 1.0 to 3.0 mol $Zn^{++}$/mol GH.

17. A process according to claim 15 wherein the concentration of $Zn^{++}$ is from 1.1 to 2.2 mol $Zn^{++}$/mol GH.

18. A process according to claim 15 wherein the concentration of $Zn^{++}$ is from 1.2 to 2.0 mol $Zn^{++}$/mol GH.

19. A process according to claim 3, wherein the growth hormone is human growth hormone (hGH) or a derivative thereof.

20. A process according to claim 3, wherein the temperature in step b) is from about 4 to about 25° C.

21. A process according to claim 1, wherein the pH in step a) is from 6.0 to 6.5.

* * * * *